(12) United States Patent
Folz et al.

(10) Patent No.: US 6,258,984 B1
(45) Date of Patent: *Jul. 10, 2001

(54) PROCESS FOR THE PREPARATION OF 4-ALKYLSULFONYL-1-ALKYL-2-CHLOROBENZENES AND SIMILAR COMPOUNDS

(75) Inventors: Georg Folz; Theodor Papenfuhs, both of Frankfurt am Main (DE)

(73) Assignee: Clariant GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/107,661
(22) PCT Filed: Jan. 31, 1992
(86) PCT No.: PCT/EP92/00205
  § 371 Date: Aug. 12, 1993
  § 102(e) Date: Aug. 12, 1993
(87) PCT Pub. No.: WO92/14700
  PCT Pub. Date: Sep. 3, 1992

(30) Foreign Application Priority Data

Feb. 14, 1991 (DE) .................................. 41 04 393

(51) Int. Cl.$^7$ .......................... C07C 317/14; C07C 313/04
(52) U.S. Cl. .............................. 568/28; 562/125
(58) Field of Search ................... 568/28; 562/125

(56) References Cited

U.S. PATENT DOCUMENTS

| 4,012,442 | 3/1977 | Blank et al. ............... 260/543 R |
| 4,675,447 | 6/1987 | Ludvik ............................ 568/657 |
| 4,825,005 | * 4/1989 | Frey et al. ..................... 568/657 |

FOREIGN PATENT DOCUMENTS

| 133000 | 7/1902 | (DE) . |
| 0 115 328 | 8/1984 | (EP) . |
| 0 258 190 | 3/1988 | (EP) . |
| 162064 | 3/1988 | (IN) . |
| 165445 | 10/1989 | (IN) . |
| 91/07384 | 5/1991 | (WO) . |

OTHER PUBLICATIONS

Methoden Der Organischen Chemie, (Houben–Weyl), Vol. IX, pp. 306–307 (1955).

* cited by examiner

Primary Examiner—Floyd D. Higel
(74) Attorney, Agent, or Firm—Connolly Bove Lodge & Hutz LLP

(57) ABSTRACT

Process for the preparation of 4-alkylsulfonyl-1-alkyl-2-chlorobenzenes and like compounds.

A process for the preparation of 4-alkyl($C_1$–$C_4$)-sulfonyl-1-alkyl-2-chlorobenzenes, in very good yields and with high selectivity by selectively chlorinating a p-alkyl-benzenesulfonyl chloride with gaseous chlorine in the presence of a chlorine carrier at 50° C. to 100° C. to give a compound of the formula

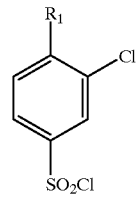

in which $R_1$ is an alkyl ($C_1$–$C_4$) group, subsequently reducing the latter in an aqueous medium at a pH of 8 to 10 with sodium hydrogen sulfite or sodium sulfite at 40 to 90° C. to give a compound of the formula

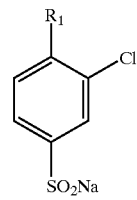

and reacting the latter with alkyl($C_1$–$C_4$) chloride in the presence of an acid binder at 80 to 150° C., and also compounds of the last mentioned formula which, instead of the —$SO_2$Na group contain the —$SO_2$X group (X=hydrogen atom or alkali metal atom).

13 Claims, No Drawings

PROCESS FOR THE PREPARATION OF 4-ALKYLSULFONYL-1-ALKYL-2-CHLOROBENZENES AND SIMILAR COMPOUNDS

The invention relates to a process for the preparation of 4-alkyl($C_1$–$C_4$)-sulfonyl-1-alkyl($C_1$–$C_4$)-2-chlorobenzenes, in particular 4-methylsulfonyl-1-methyl-2-chlorobenzene, where the 4-alkyl($C_1$–$C_4$)-3-chlorobenzenesulfinic acids formed as intermediates in this process and the end products obtained, except for 4-methylsulfonyl-1-methyl-2-chlorobenzene (U.S. Pat. No. 4,675,447), are novel compounds.

The compounds are valuable intermediates for pesticides and herbicides.

Preparation of 4-alkylsulfonyl-1-alkyl-2-chlorobenzenes by chlorination of 4-alkylsulfonylalkylbenzenes with sulfuryl chloride in the presence of antimony chloride as a catalyst is known (U.S. Pat. No. 4,675,447).

Disadvantages of this are the use of relatively expensive sulfuryl chloride, substantial production of the environmentally polluting sulfur dioxide and the preparation of isolated, dry 4-alkylsulfonylalkylbenzenes.

It has now surprisingly been found that 4-alkylsulfonyl-1-alkyl-2-chlorobenzenes of the formula (4)

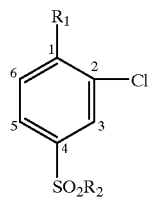
(4)

in which $R_1$ and $R_2$ are identical or different alkyl groups having 1 to 4 carbon atoms, may be prepared, avoiding the disadvantages associated with the process of the prior art, in very good yields and in high selectivity by selectively chlorinating 1 mol of a p-alkylbenzene-sulfonyl chloride of the formula (1)

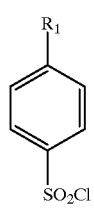
(1)

in which $R_1$ has the meaning given above, with at least 1 mol of gaseous chlorine in the presence of a chlorine carrier, such as for example iron(III) chloride or iron(III) chloride and iodine, at temperatures of about 50° C. to about 100° C., preferably of about 70° C. to about 80° C. to give the compound of the formula (2)

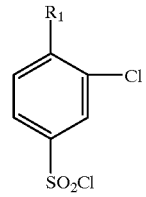
(2)

in which $R_1$ has the meaning given above, reducing the latter exclusively in an aqueous medium at a pH of about 8 to 10 with 1 to about 1.2 mol, preferably 1.1 mol, of sodium hydrogen sulfite or sodium sulfite at temperatures of about 40 to about 90° C., preferably of about 50 to about 65° C., to give a compound of the formula (3)

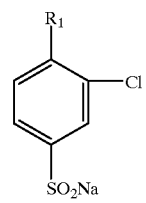
(3)

in which $R_1$ has the meaning given above, and reacting the latter with 1 to about 2.2 mol, preferably about 1.25 to about 1.90 mol, particularly preferably about 1.50 to about 1.75 mol, of alkyl($C_1$–$C_4$) chloride, in the presence of an acid binder, preferably magnesium oxide, to give the compound of the formula (4) mentioned above, at temperatures of about 80 to about 150° C.

The process according to the invention is carried out in detail as described below.

a) Chlorination:

Chlorination of the p-alkyl ($C_1$–$C_4$)-benzenesulfonyl chloride advantageously is carried out in the absence of solvents by passing through elemental chlorine at about 50–100° C., preferably at 70–80° C., with the use of about 0.1 to about 1%, preferably about 0.5%, of a catalyst mixture of 75% of iron(III) chloride and 25% of iodine. Chlorination is terminated at a degree of monochlorination of approximately 100%. (End point determination via GC). The resulting product contains, in addition to traces of the starting compound, only very small quantities of the dichloro compound. The chlorination product can be used for further processing in the form in which it occurs; however, it can also be washed, distilled or fractionated. The yield of 3-chloro-4-alkyl($C_1$–$C_4$)benzene-sulfonyl chlorides is virtually quantitative.

b) Reduction:

Reduction of the 2-chloro-4-alkyl($C_1$–$C_4$) benzenesulfonyl chlorides obtained according to a) to the 4-alkyl($C_1$–$C_4$)-3-chlorobenzenesulfinic acids can be carried out by a method known per se (cf. Houben-Weyl, Vol. 9, pp. 304–311). The reduction is advantageously carried out using $NaESO_3$+NaOH, preferably using sodium sulfite+NaOH. The reduction is optimally carried out in an aqueous medium by simultaneously adding 2-chloro-4-alkylbenzene-sulfonyl chloride (in the molten state) and sodium hydroxide solution (commercially available 35% strength) dropwise to a solution of sodium sulfite with pH monitoring at from about 8 to about 10. The sulfonyl chloride can also be added to the sulfite solution, and the sodium hydroxide solution can be added with the pH maintained at about 8 to about 10. The concentration of the sulfite solution can vary between about 10 and about 30%, preference being given to an approximately 15% strength solution. The amount of sulfite varies between the theoretical amount and an excess of about 20%, an excess of about 10% being most expedient. The reaction proceeds at a temperature of about 40 to about 90° C., preferably between about 50 and about 65° C. The reduction is complete when the pH remains constant at a value of about 8 to about 10. The sodium salt of the 4-alkyl-($C_1$–$C_4$)-3-chlorobenzenesulfinic acid crystallizes out from the solution at about 45° C. The compound can be further processed without intermediate isolation.

c) Alkylation:

Alkylation of the 4-alkyl($C_1$–$C_4$)-3-chlorobenzenesulfinic acids (Na salts) obtained according to b) to give the corresponding 4-alkyl ($C_1$–$C_4$)-sulfonyl-2-chloroalkyl-benzenes takes place using alkyl($C_1$–$C_4$) chlorides, preferably methyl chloride. To carry out this reaction, the reduction solution obtained according to b) (isolation of the sulfinate is not necessary) is placed in a pressure apparatus (autoclave), and the corresponding alkyl($C_1$–$C_4$) chlorides and an acid binder, preferably magnesium oxide, for neutralization of the hydrogen chloride produced from the hydrolysis of the excess alkyl($C_1$–$C_4$) chloride, are added. The amount of the alkyl($C_1$–$C_4$) chlorides used varies in the range from about 100 to about 220% of theory, advantageously between about 125 and about 190%, particularly preferably between about 150 and about 175%. The alkyl chlorides can be added all at once, or in portions or continuously during the reaction. The reaction temperatures for methylation are in the range from about 80 to about 100° C. With the use of alkyl($C_4$) chlorides, a reaction temperature of about 150° C. is required.

The acid binders used can be, apart from magnesium oxide, for example, the hydroxide, carbonate or hydrogen carbonate of metals selected from the group comprising lithium, sodium, potassium, rubidium, caesium, magnesium, calcium, barium and strontium, or mixtures of these compounds.

The following examples are intended to illustrate the process according to the invention in more detail, without restricting it thereto.

EXAMPLE 1

(Clorination)

Preparation of 2-Chloro-P-Toluenesulfonyl Chloride 576 g (3 mol) of p-toluenesulfonyl chloride are melted in a chlorination apparatus. After addition of 7 g of iron(III) chloride and 2 g of iodine, elemental chlorine was passed in at 75–80° C. at a rate of 5 l of $Cl_2$/h, until practically 100% monochlorination was achieved (GC analysis).

The product, after flushing out the residual chlorine and HCl, can be used in the crude state; however, it can also be washed and, if required, distilled.

The yield is about 100% of theory.

Purity: ≧97% (small amount of starting compound and dichloro compound also present)

EXAMPLE 2

(Reduction)

Preparation of 4-Methyl-3-Chlorobenzenesulfinic Acid (Na Salt)

2350 ml of water and 420 g (3.3 mol) of sodium sulfite (=15.1% strength $Na_2SO_3$ solution) are introduced into a stirrer apparatus equipped with 2 dropping funnels and a pH electrode, and the mixture is heated to 50–55° C. In the course of about 2 h, 677 g (3 mol) of 2-chloro-p-toluenesulfonyl chloride are run in and simultaneously 690 g of NaOH (35% strength) are added dropwise so that a pH of 8–10 is maintained. The temperature is allowed to rise to 65° C. The reaction is completed when the pH remains constant at 8–10. The sodium sulfinate is in solution at 60–65° C., and crystallizes out from about 55° C.

It is expedient to use the product thus obtained in the next step (alkylation) without intermediate isolation.

EXAMPLE 3

(Alkylation)

Preparation of 4-Methylsulfonyl-1-Methyl-2-Chlorobenzene

The solution of 4-methyl-3-chlorobenzenesulfinic acid (Na salt) obtained according to Example 2 is introduced into an autoclave and 45 g of magnesium oxide are added. The autoclave is then sealed. Subsequently, 270 g (5.3 mol; 175% of theory) of methyl chloride are injected, the pressure climbing to 6–7 bar, and the mixture is heated in the course of about 1 h to 90–95° C.; at 80–85° C. the pressure reaches a maximum of 13–14 bar, then subsequently decreases to 4–5 bar because of methyl chloride consumption. The mixture is stirred for a further 4 h.

After the mixture has cooled, the pressure is reduced, and the reaction mixture is acidified using 225 g of hydrochloric acid (30% strength). Subsequently the mixture is stirred at 90–95° C. for approximately 1 h to dissolve all the magnesium oxide and any by-products. The product is crystallized out by cooling, and is isolated by filtration.

The yield is about 90% (calculated over the reduction and methylation steps).

Content: ≧97%

Melting point: 88–91° C.

EXAMPLE 4

(Alkylation)

Preparation of 4-Ethylsulfonyl-1-Methyl-2-Chlorobenzene

The solution of 4-methyl-3-chlorobenzenesulfinic acid (Na salt) obtained according to Example 2 is introduced into an autoclave and 45 g of magnesium oxide are added. The autoclave is then sealed, and 342 g (5.3 mol; 175% of theory) of ethyl chloride are injected, the pressure climbing to 4.5 bar. The mixture is heated in the course of 1 h to 130–140° C., the pressure reaching a maximum of approximately 12 bar, then subsequently decreasing to approximately 5–6 bar because of the ethylene chloride consumption. The mixture is subsequently stirred for a further 4–5 h.

After the mixture has cooled, the pressure is reduced, and the reaction mixture is acidified using 225 g of hydrochloric acid (30% strength). Subsequently the mixture is stirred at 90–95° C. for approximately 1 h to dissolve all the magnesium oxide and any by-products. The product is crystallized out by cooling, and is isolated by filtration.

The yield is about 90% (calculated over the reduction and ethylation steps).

Content: ≧97%

Melting point: 50–52° C.

$C_9H_{11}ClO_2S$: calculated: C 49.38%; H 5.029%; Cl 16.23% found : C 49.19%; H 5.014%; Cl 16.37%

EXAMPLE 5

(Chlorination)

Preparation of 3-Chloro-4-Ethylbenzenesulfonyl Chloride

The procedure described in Example 1 was followed, with the sole difference that in this case 615 g (3 mol) of 4-ethylbenzenesulfonyl chloride were used.

The yield is about 100% of theory.
Purity: ≧96% (small amount of starting compound and dichloro compound also present)
Freezing point: 21–22° C.
Boiling point (2.5–3 mmHg): 129–130° C.
$C_7H_8Cl_2O_2S$: calculated: C 40.18%; H 3.37%; Cl 29.65% found: C 40.02%; H 3.29%; Cl 29.73%

EXAMPLE 6
(Reduction)
Preparation of 3-Chloro-4-Ethylbenzenesulfinic Acid (Na Salt)

The procedure described in Example 2 was followed, with the sole difference that in this case 718 g (3 mol) of 3-chloro-4-ethylbenzenesulfonyl chloride were used.

The sodium sulfinate only crystallized out at low temperature.

It is expedient to use the product thus obtained in the next step (alkylation) without intermediate isolation (cf. Examples 7 and 8; yield also quoted there).

EXAMPLE 7
(Alkylation)
Preparation of 4-Methylsulfonyl-1-Ethyl-2-Chlorobenzene The solution of 3-chloro-4-ethylbenzenesulfinic acid (Na salt) obtained according to Example 6 is introduced into an autoclave. Subsequently, the procedure described in Example 3 is followed.

The yield is about 88% of theory (calculated over the reduction and methylation steps).
Content: ≧96%
Melting point: 58–60° C.
$C_9H_{11}ClO_2S$: calculated: C 49.427%; H 5.07%; Cl 16.211% found: C 49.29%; H 5.03%; Cl 16.32%

EXAMPLE 8
(Alkylation)
Preparation of 4-Ethylsulfonyl-1-Ethyl-2-Chlorobenzene The solution of 3-chloro-4-ethylbenzenesulfinic acid (Na salt) obtained according to Example 6 is introduced into an autoclave. Subsequently, the procedure described in Example 4 is followed. Owing to the lower freezing point of the product, it is separated as a liquid at 40–50° C. (organic phase underneath) and, following addition of approximately 1000 ml of water, distilled (1.5 mm Hg, 153–155° C.).

The yield is about 80% of theory (calculated over the reduction and ethylation steps).
Content: ≧96%
Melting point: 36–37° C.
$C_{10}H_{13}ClO_2S$: calculated: C 51.609%; H 5.633%; Cl 15.233% found: C 51.53%; H 5.49%; Cl 15.37%

What is claimed is:
1. A process for the preparation of a 4-alkyl($C_1$–$C_4$)-sulfonyl-1-alkyl-2-chlorobenzene of the formula (4)

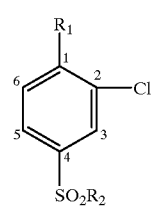

(4)

in which $R_1$ and $R_2$ are identical or different alkyl groups having 1 to 4 carbon atoms, which comprises selectively chlorinating 1 mol of a p-alkylbenzene-sulfonyl chloride of the formula (1)

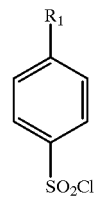

(1)

in which $R_1$ has the meaning given above, with at least 1 mol of gaseous chlorine in the presence of a chlorine carrier at temperatures of about 50° C. to about 100° C. to give the compound of the formula (2)

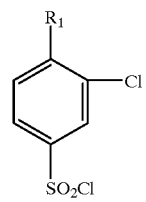

(2)

in which $R_1$ has the meaning given above, subsequently reducing the latter in an aqueous medium at a pH of about 8 to about 10 with 1 to about 1.2 mol of sodium hydrogen sulfite or sodium sulfite at temperatures of about 40 to about 90° C. to give a compound of the formula (3)

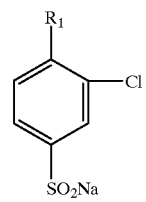

(3)

in which $R_1$ has the meaning given above, and reacting the latter with 1 to about 2.2 mol of alkyl($C_1$–$C_4$) chloride in the presence of an acid binder at temperatures of about 80 to about 150° C. to give the compound of the formula (4) mentioned above.

2. The process as claimed in claim 1, wherein the chlorination is carried out at temperatures of about 70 to about 80° C.

3. The process as claimed in claim 1 wherein the chlorination is carried out in the presence of iron(III) chloride.

4. The process as claimed in claim 1 wherein the chlorination is carried out in the presence of iron(III) chloride and iodine.

5. The process as claimed in claim 1, wherein 1 mole of the compound of formula (2) which is 3-chloro-4-alkylbenzenesulfonyl chloride is reduced with 1.1 mol of sodium hydrogen sulfite or sodium sulfite.

6. The process as claimed in claim 1, wherein the compound of formula (2) which is 3-chloro-4-alkylbenzenesulfonyl chloride is reduced at temperature of about 50 to about 65° C.

7. The process as claimed in claim 1, wherein 1 mole of the compound of formula (3) which is sodium 4-alkyl ($C_1$–$C_4$)-3-chlorobenzenesulfinate is alkylated using about 1.25 to about 1.90 mol of alkyl($C_1$–$C_4$) chloride.

8. The process as claimed in claim 1, wherein 1 mol of the compound of formula (3) which is sodium 4-alkyl($C_1$–$C_4$)-3-chlorobenzenesulfinate is alkylated using about 1.50 to about 1.75 mol of alkyl($C_1$–$C_4$) chloride.

9. The process as claimed in claim 1, wherein the compound of formula (3) which is sodium 4-alkyl($C_1$–$C_4$)-3-chlorobenzenesulfinate is alkylated in the presence of magnesium oxide as an acid binder.

10. The process as claimed in claim 1, wherein the compound of formula (3) which is sodium 4-methyl-3-chlorobenzenesulfinate is methylated using methyl chloride at temperatures of about 80 to about 100° C.

11. The process as claimed in claim 1, wherein the purity is greater than or equal to 96%.

12. The process as claimed in claim 11, wherein the yield is about 90% calculated over the reduction and ethoxylation steps.

13. The process as claimed in claim 1, wherein the yield is about 90% calculated over the reduction and ethoxylation steps.

* * * * *